(12) United States Patent
Soga et al.

(10) Patent No.: US 7,101,068 B2
(45) Date of Patent: Sep. 5, 2006

(54) WATER CLOUD EVALUATING DEVICE FOR VEHICLE LIGHTING FIXTURE

(75) Inventors: Shigeyuki Soga, Shizuoka (JP); Akira Kaneko, Shizuoka (JP); Masahiro Ikegaya, Shizuoka (JP); Masaki Hagiwara, Shizuoka (JP); Makoto Ohishi, Shizuoka (JP)

(73) Assignee: Koito Manufacturing Co., Ltd., Tokyo (JP)

( * ) Notice: Subject to any disclaimer, the term of this patent is extended or adjusted under 35 U.S.C. 154(b) by 253 days.

(21) Appl. No.: 10/761,346

(22) Filed: Jan. 22, 2004

(65) Prior Publication Data
US 2004/0149054 A1   Aug. 5, 2004

(30) Foreign Application Priority Data
Jan. 23, 2003  (JP) .......................... P.2003-014655
Jan. 23, 2003  (JP) .......................... P.2003-014656

(51) Int. Cl.
*B60Q 1/00* (2006.01)
*G01N 17/00* (2006.01)

(52) U.S. Cl. ..................................... 362/547; 73/865.6

(58) Field of Classification Search ................ 362/294, 362/459, 547; 73/865.6; 356/121, 122
See application file for complete search history.

(56) References Cited

U.S. PATENT DOCUMENTS
6,332,370 B1 *  12/2001  Fukai ........................ 73/865.6

FOREIGN PATENT DOCUMENTS
JP         2001-165819 A      6/2001

* cited by examiner

*Primary Examiner*—Stephen F Husar
(74) *Attorney, Agent, or Firm*—Sughrue Mion, PLLC

(57) ABSTRACT

A water cloud evaluating device includes a partition member for partitioning an outer space of the vehicle lighting fixture into a front space and a rear space, vehicle outside environment simulation setting means and vehicle inside environment simulation setting means. In the bench test, the water cloud evaluation is made in the artificial environment close to the state where the vehicle lighting fixture is mounted on the actual vehicle. The partition member is formed with an opening portion in a sheet that is easily cuttable by a knife or the like. A water spray unit, an illumination unit and an air flow generating unit are made movable as the simulation setting units comprising both the simulation setting means.

20 Claims, 12 Drawing Sheets

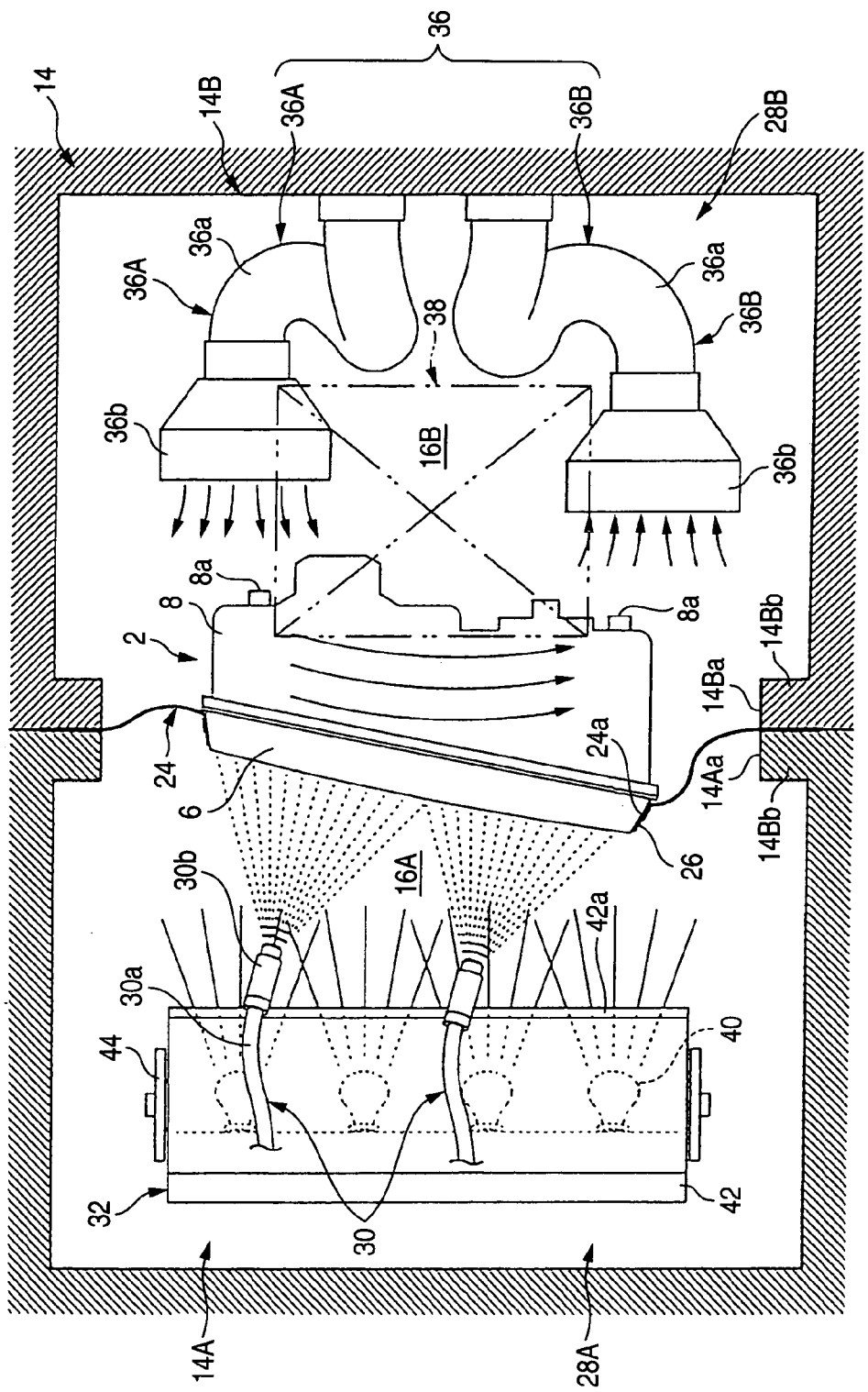

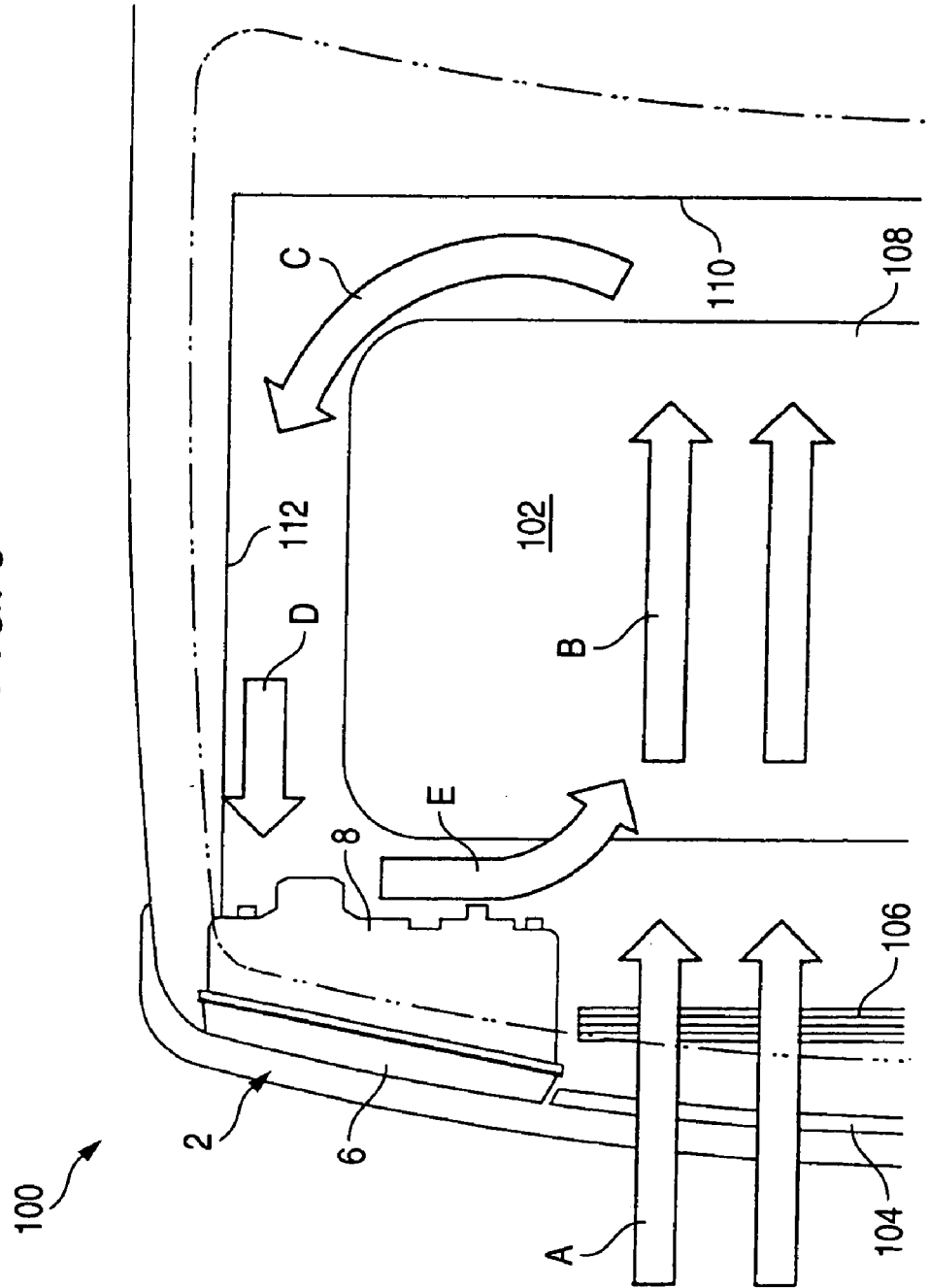

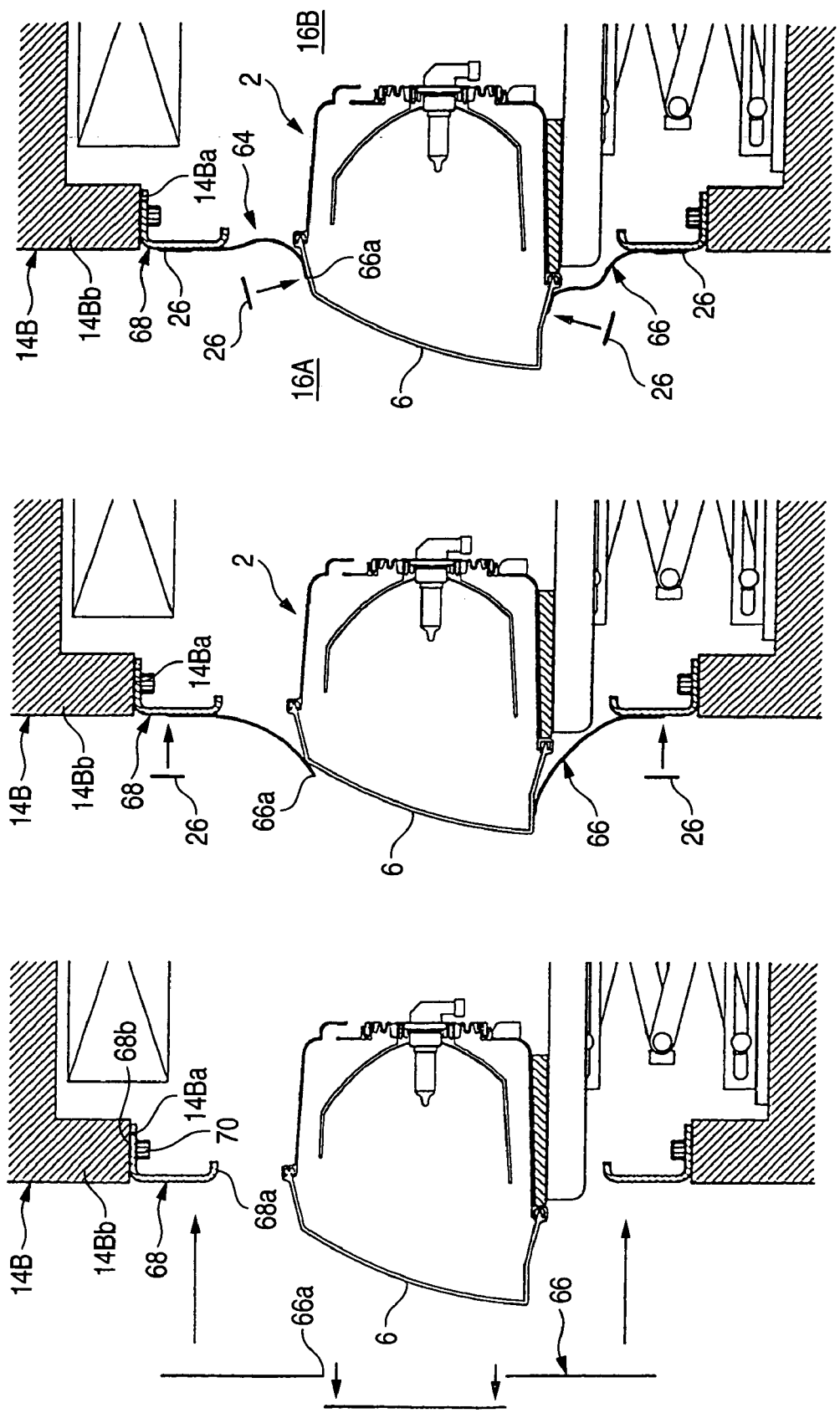

WATER CLOUD EVALUATING DEVICE FOR VEHICLE LIGHTING FIXTURE

The present invention claims foreign priority to Japanese Patent Application Nos. 2003-014655 and 2003-014656, both of which were filed on Jan. 23, 2003, the contents of which is incorporated herein by reference.

BACKGROUND OF THE INVENTION

1. Field of the Invention

The present invention relates to a water cloud evaluating device for evaluating a water cloud occurring within a lighting chamber for a vehicle lighting fixture.

2. Description of the Related Art

In the related art vehicle lighting fixture, the lighting chamber is typically comprised of a translucent cover and a lamp body. On the rear part of the lamp body, vent holes are often formed to connect the lighting chamber to an outer space of the lighting fixture, thus preventing changes in the atmospheric pressure within the lighting chamber from occurring due to repeated light usage. As a result, a water cloud (i.e., a cloud formed in the lighting chamber due to moisture) is less likely to occur within the lighting chamber.

On the other hand, in this related art vehicle lighting fixture, the water content permeating from the lighting fixture outer space into the lighting chamber through the vent holes forms as condensation (e.g., dew droplets) on an inner surface of a lens to produce a water cloud, unless the structure or arrangement of the vent holes is fully taken into consideration.

Since this related art water cloud is not typically evaluated very precisely by benchmark testing, the water cloud evaluation is made by mounting the lighting fixture on the actual vehicle and driving the vehicle. However, with such an evaluation method, it is necessary to mount the lighting fixture on the actual vehicle. Therefore, it is not easy to perform repeated water cloud evaluation tests, and it is difficult to acquire the precise evaluation results in a short time.

On the contrary, in JP-A-2001-165819, the contents of which is incorporated herein by reference, a water cloud evaluating device was described, comprising a partition member for partitioning a lighting fixture outer space into a front space and a rear space around the outer circumferential portion of a lighting fixture, vehicle outside environment simulation setting means for simulatively setting the front space in a predetermined vehicle outside environment, and vehicle inside environment simulation setting means for simulatively setting the rear space in a predetermined vehicle inside environment.

Employing the water cloud evaluating device as described in the JP-A-2001-165819, precise water cloud evaluation results are acquired by the bench test. However, the following problems arise.

For example, but not by way of limitation, the vehicle lighting fixture is typically varied in shape, dimensions, amount of circulation to the rear side of the lighting fixture, and inclination angle of the translucent cover, depending on the shape of a vehicle body on which the lighting fixture is mounted. Therefore, when the partition member is made from a rigid plate as in the water cloud evaluating device described in the JP-A-2001-165819, it is difficult to appropriate the partition member fabricated for one vehicle lighting fixture to another vehicle lighting fixture. Accordingly, when the water cloud evaluation is made for a new vehicle lighting fixture, it is necessary to fabricate a new partition member in accordance with the shape of the vehicle lighting fixture. Thus, a related art problem results in the water cloud evaluation requiring more time and cost.

Further, in this related art water cloud evaluating device, a water spray unit and an illumination unit are provided as the simulation setting units comprising the vehicle outside simulation setting means, and an air flow generating unit and a temperature/humidity control unit are provided as the simulation setting units comprising the vehicle inside simulation setting means. Since these simulation setting units are stationary, it is not easy to precisely set the front space in a desired vehicle outside environment by simulation, or to precisely set the rear space in a desired vehicle inside environment by simulation.

In this regard, there is yet room for improvement to obtain the water cloud evaluation result a thigh precision. Also, since each simulation setting unit is stationary, there is a related art problem in that it is difficult to perform the operation for installing or removing the vehicle lighting fixture to be evaluated.

SUMMARY OF THE INVENTION

The present invention has been achieved in the light of the above-mentioned problems. However, other problems may also be solved by the present invention, or alternatively, the present invention may not solve any problems at all. It is a first object of the invention to provide a water cloud evaluating device for vehicle lighting fixture in which the precise water cloud evaluation results are obtained by a bench test, and the evaluation test is made efficiently and at lower cost.

It is a second object of the invention to provide a water cloud evaluating device for vehicle lighting fixture in which the precise water cloud evaluation results are obtained by the bench test, and the operability at the time of evaluation test is enhanced.

This invention enhances the universality of the lighting fixture by designing the constitution of the partition member to achieve the above first object.

That is, according to a first exemplary, non-limiting embodiment of the present invention, there is provided a water cloud evaluating device for evaluating the water cloud occurring within a lighting chamber for a vehicle lighting fixture, the lighting chamber being comprised of a translucent cover and a lamp body, the lamp body being formed with vent holes for communicating the lighting chamber to an outer space of the lighting chamber. The evaluating device includes a partition member for partitioning the outer space of the lighting fixture into a front space and a rear space around the outer circumferential portion of the lighting fixture, vehicle outside environment simulation setting means for simulatively setting the front space in a predetermined vehicle outside environment, and vehicle inside environment simulation setting means for simulatively setting the rear space in a predetermined vehicle inside environment. The partition member has a predetermined opening portion formed in an easily cuttable sheet.

Also, according to a second exemplary, non-limiting embodiment of the present invention, there is provided a water cloud evaluating device for evaluating the water cloud occurring within a lighting chamber for a vehicle lighting fixture, the lighting chamber being comprised of a translucent cover and a lamp body, the lamp body being formed with vent holes for communicating the lighting chamber to an outer space of the lighting fixture. The evaluating device comprises a partition member for partitioning the outer space of the lighting fixture into a front space and a rear space around the outer circumferential portion of the lighting fixture, vehicle outside environment simulation setting means for simulatively setting the front space in a predetermined vehicle outside environment, and vehicle inside environment simulation setting means for simulatively setting the rear space in a predetermined vehicle inside environment. The partition member has a predetermined opening portion formed in a flexible sheet.

The vehicle lighting fixture to be evaluated for water cloud by the "water cloud evaluating device" is not limited to a specific kind of lighting fixture, but, for example but not by way of limitation, may be a head lamp or a marker lamp.

The "front space" and the "rear space" may be any combination of a closed space and an open space.

The partitioning position of the partition member on the "outer circumferential portion of lighting fixture" is not specifically limited, but may be the position on the outer circumferential portion of the translucent cover or the lamp body, or the position set up to extend over both the translucent cover and the lamp body. In this case, from the viewpoint that the water cloud evaluation is made in the environment of the vehicle fixture outer space as close to the actual vehicle mounted state as possible, it is preferable that when the vehicle lighting fixture is mounted on the vehicle body, the partitioning position is set up along the boundary line between a portion of the vehicle lighting fixture exposed to the outer space of the vehicle body and an unexposed portion. The position of the boundary line is typically set near a joined face between the translucent cover and the lamp body.

The "predetermined vehicle outside environment" and the "predetermined vehicle inside environment" may be any of the vehicle outside environments and vehicle inside environments that are supposed on the actual vehicle, for example, the environment in the state where the vehicle is running, stopped, running in the rainy weather, running during the duration of sunshine, conveyed in the car wash, or any combination thereof. In this case, a specific example of the "predetermined vehicle inside environment" is the environment in the engine room, or the trunk room.

The "sheet" according to the first exemplary, non-limiting embodiment of the present invention is not specifically limited in terms of size, shape, thickness and material, as far as it is easily cuttable, and may be made of vinyl chloride, vinylidene chloride or polyethylene, or any equivalent thereof. Also, the "opening portion" of the sheet is not specifically limited in terms of size and shape. The "easily cuttable" as herein used means to be cuttable by cutting means such as a knife or the scissors. In practice, when the opening portion is formed in the sheet, other cutting means than the knife or scissors may be employed.

The "sheet" according to the second exemplary, non-limiting embodiment of the present invention is not specifically limited in terms of size, shape, thickness and material, as far as it is flexible, and may be made of synthetic rubber or thermoelastomer. Also, the "opening portion" of the sheet is not specifically limited in terms of size and shape.

As described above, the water cloud evaluating device for vehicle lighting fixture according to the exemplary, non-limiting embodiments of the present invention comprises the partition member for partitioning the outer space of the vehicle lighting fixture into the front space and the rear space around the outer circumferential portion of the lighting fixture, vehicle outside environment simulation setting means for simulatively setting the front space in a predetermined vehicle outside environment, and vehicle inside environment simulation setting means for simulatively setting the rear space in a predetermined vehicle inside environment. Therefore, the water cloud evaluation is made in the artificial environment of the lighting fixture outer space close to the state where the vehicle lighting fixture is mounted on the actual vehicle, although the vehicle lighting fixture is not mounted on the actual vehicle, whereby the water cloud evaluation results are obtained at high precision. Further, the water cloud evaluation is made by the bench test in the above way, and thereby can be repeated many times in a short time to reduce the cost.

In this water cloud evaluating device for vehicle lighting device according to the first exemplary, non-limiting embodiment of the present invention, the partition member is formed with the opening portion in the sheet that is easily cuttable, bringing about the following operation effect.

A part of the sheet is cut out by the knife or the like to form the opening portion corresponding to the vehicle lighting fixture to be evaluated, whereby the partition member is easily produced for the vehicle lighting fixture with the outer circumferential portion of the lighting fixture having different shape or size. In this case, the sheet having flexibility is easily disposed according to the shape of the outer circumferential portion of the lighting fixture. And the sheet which is easily cuttable by the knife or the like is generally quite cheaper than the rigid plate. Thus, the partition member has a reduced manufacturing cost.

This easily cuttable sheet may be subjected to the evaluation test when the opening portion is cut out, or preferably when the sheet is fixed around the opening portion to the outer circumference of lighting fixture for the vehicle lighting fixture by the adhesive tape or adhesive agent, from the view point of performing the function as the partition member.

On the other hand, in the water cloud evaluating device for vehicle lighting device according to the second exemplary, non-limiting embodiment of the present invention, the partition member is formed with the opening portion in the flexible sheet, bringing about the following operation effect.

The circumferential portion of the opening portion in the sheet is fitted over the outer circumferential portion of lighting fixture for the vehicle lighting fixture, while being elastically deformed, whereby the partition member is easily formed. In this case, for the vehicle lighting fixture in which the outer circumferential portion of lighting fixture has different shape or size, the same sheet can be appropriated to form the partition member in a range where the sheet is elastically deformed, whereby there is a substantially reduced need for producing the new partition member, thus greatly reducing the manufacturing cost of the partition member.

In this way, in the water cloud evaluating device for evaluating the water cloud occurring within the lighting chamber in the vehicle lighting fixture, the water cloud evaluation results are obtained at high precision by the bench test, and the evaluation test is made efficiently at a low cost.

In each above described exemplary, non-limiting embodiment of the present invention, the partition member may be comprised of the sheet and the rigid plate for supporting its circumferential portion, but not comprised of the sheet alone. By taking this constitution, the sheet is reduced in size, and the amount of material used to make the sheet is reduced. In this case, since the rigid plate is appropriated for the vehicle lighting fixture in which the outer circumferential portion of the lighting fixture has a different shape or size it is only necessary to replace the sheet of smaller size, when the evaluation test is made for the new vehicle lighting fixture. Thereby, the water cloud evaluation is made at lower cost.

In each exemplary, non-limiting embodiment of the present invention as described above, if the partition member is made of an opaque material to the visible and near infrared radiation, it is effective to suppress the influence of radiant heat from the illumination unit on the temperature of the rear space, when the illumination unit is provided in the front space as the simulation setting unit comprising the vehicle outside environment simulation setting means.

Further, the exemplary, non-limiting embodiments of this invention makes movable at least one of plural simulation setting units comprising vehicle outside environment simulation setting means and vehicle inside environment simulation setting means to achieve the above second object.

According to a third exemplary, non-limiting embodiment of the present invention, there is provided a water cloud evaluating device for vehicle lighting fixture that evaluates the water cloud occurring within a lighting chamber for a vehicle lighting fixture, the lighting chamber being comprised of a translucent cover and a lamp body, the lamp body being formed with vent holes for communicating the lighting chamber to an outer space of the lighting chamber. The evaluating device comprises a partition member for partitioning the outer space of the lighting fixture into a front space and a rear space around the outer circumferential portion of the lighting fixture, vehicle outside environment simulation setting means for simulatively setting the front space in a predetermined vehicle outside environment, and vehicle inside environment simulation setting means for simulatively setting the rear space in a predetermined vehicle inside environment. The vehicle outside environment simulation setting means comprises at least one simulation setting unit provided in the front space, and the vehicle inside environment simulation setting means comprises at least one simulation setting unit provided in the rear space. At least one of plural simulation setting units comprising the vehicle outside environment simulation setting means and the vehicle inside environment simulation setting means is movable.

The vehicle lighting fixture to be evaluated for water cloud by the "water cloud evaluating device" is not limited to a specific kind of lighting fixture, but may be a head lamp or a marker lamp.

The "front space" and the "rear space" may be at least one of a closed space and an open space.

The partitioning position of the partition member on the "outer circumferential portion of lighting fixture" is not specifically limited, but may be the position on the outer circumferential portion of the translucent cover or the lamp body, or the position set up to extend over both the translucent cover and the lamp body. In this case, from the viewpoint that the water cloud evaluation is made in the environment of the vehicle fixture outer space as close to the actual vehicle mounted state as possible, it is preferable that when the vehicle lighting fixture is mounted on the vehicle body, the partitioning position is set up along the boundary line between a portion of the vehicle lighting fixture exposed to the outer space of the vehicle body and an unexposed portion. The position of the boundary line is typically set near a joined face between the translucent cover and the lamp body.

The "predetermined vehicle outside environment" and the "predetermined vehicle inside environment" may be any of the vehicle outside environments and vehicle inside environments that are supposed on the actual vehicle, for example, but not by way of limitation, the environment in the state where the vehicle is running, stopped, running in the rainy weather, running during the duration of sunshine, conveyed in the car wash, or in combination thereof. In this case, a specific example of the "predetermined vehicle inside environment" is the environment of the engine room, or the trunk room.

The "vehicle outside environment simulation setting means" is not specifically limited in constitution, as long as it comprises at least one simulation setting unit provided in the front space and is able to set the front space in a predetermined vehicle outside environment by simulation. The vehicle outside environment simulation setting means may comprise one kind of simulation setting unit alone, or plural kinds of simulation setting units. Also, one or more simulation setting units of the same kind may be provided. The "simulation setting units" comprising the vehicle outside environment simulation setting means may include a water spray unit, an illumination unit and a blast unit, for example but not by way of limitation.

Similarly, the "vehicle inside environment simulation setting means" is not specifically limited in the constitution, as long as it comprises at least one simulation setting unit provided in the rear space and is able to set the rear space in a predetermined vehicle inside environment by simulation. The vehicle inside environment simulation setting means may comprise one kind of simulation setting unit alone, or plural kinds of simulation setting units. Also, one or more simulation setting units of the same kind may be provided. The "simulation setting units" comprising the vehicle inside environment simulation setting means may include an air flow generating unit, a temperature control unit and a humidity control unit, for example but not by way of limitation.

The "at least one of plural simulation setting units comprising the vehicle outside environment simulation setting means and the vehicle inside environment simulation setting means is configured to be movable," means that one or both of the simulation setting units are movable when each of the vehicle outside environment simulation setting means and the vehicle inside environment simulation setting means comprises a single simulation setting unit, or that at least one of the simulation setting units are movable when the vehicle outside environment simulation setting means or the vehicle inside environment simulation setting means comprises plural simulation setting units. In this case, each simulation setting unit is not specifically limited in the moving form, and can be moved by the linear reciprocating motion or rotation motion, for example.

As described above, the water cloud evaluating device for vehicle lighting fixture according to the present invention comprises the partition member for partitioning the outer space of the vehicle lighting fixture into the front space and the rear space around the outer circumferential portion of the lighting fixture, vehicle outside environment simulation setting means for simulatively setting the front space in a predetermined vehicle outside environment, and vehicle inside environment simulation setting means for simulatively setting the rear space in a predetermined vehicle inside environment. Therefore, the water cloud evaluation is made in the artificial environment of the lighting fixture outer space close to the state where the vehicle lighting fixture is mounted on the actual vehicle, although the vehicle lighting fixture is not mounted on the actual vehicle, whereby the water cloud evaluation results are obtained at a high precision. And the water cloud evaluation is made by the bench test in the above way, and thereby can be repeated many times in a short time to reduce the cost.

In this water cloud evaluating device for vehicle lighting device according to the present invention, the vehicle outside environment simulation setting means comprises at least one simulation setting unit provided in the front space, and the vehicle inside environment simulation setting means comprises at least one simulation setting unit provided in the rear space, wherein at least one of plural simulation setting units comprising the vehicle outside environment simulation setting means and the vehicle inside environment simulation setting means is movable, bringing about the following operation effect.

The movable simulation setting unit comprising the vehicle outside environment simulation setting unit or the movable simulation setting unit comprising the vehicle inside environment simulation setting unit is appropriately moved to adjust its position or attitude, whereby the front space or rear space is easily set in the desired vehicle outside environment or inside environment by simulation, so that the water evaluation results are obtained at higher precision.

Also, in installing or removing the vehicle lighting fixture to be evaluated, the movable simulation setting unit is appropriately moved, thereby facilitating the installation or removal operation.

In this way, according to the present invention, in the water cloud evaluating device for evaluating the water cloud occurring within the lighting chamber for the vehicle lighting fixture, the precise water cloud evaluation results are obtained by the bench test, and the operability at the time of evaluation test is substantially enhanced.

In the above constitution, the simulation setting units comprising the vehicle outside environment simulation setting unit may be disposed within the first vessel formed with the rear opening portion that opens to the rear, and thus is less affected by external disturbance than disposed in open space. As a result, it is easier to set the vehicle outside environment by simulation.

In this case, the "rear opening portion" and the "front opening portion" are not specifically limited in the size or shape, as long as they have the opening area somewhat larger than the vehicle lighting fixture to be evaluated.

Also, in this case, since the partition member is provided to enclose the rear opening portion of the first vessel or the front opening portion of the second vessel, the front space or the rear space is constituted as a sealed space, whereby the vehicle outside environment or the vehicle inside environment is more easily set by simulation.

Further, in this case, at least one of the first vessel and the second vessel is configured to be movable between a position for closing the rear opening portion of the first vessel and the front opening portion of the second vessel and a position for opening them, whereby the front space and the rear space are made the sealed space at the closed position. Therefore, it is possible to more easily set the vehicle outside environment and the vehicle inside environment by simulation. Also, if the first vessel or the second vessel is configured to be movable, the simulation setting units comprising the vehicle outside environment simulation setting means or the simulation setting units comprising the vehicle inside environment simulation setting means can be moved simultaneously, thereby facilitating the operation of installing or removing the vehicle lighting fixture to be evaluated.

Additionally, if the first vessel or the second vessel is configured to be movable, the water cloud occurrence state within the lighting chamber is easily observed through the eyes at the position near the translucent cover after the evaluation test, whereby the water cloud evaluation is made at higher precision.

BRIEF DESCRIPTION OF THE DRAWINGS

The above and other objects and advantages of the present invention will become more apparent by describing in detail exemplary, non-limiting embodiments thereof with reference to the accompanying drawings, wherein like reference numerals designate like or corresponding parts throughout the several views, and wherein:

FIG. 4 is a plan cross-sectional view of the essence of FIG. 1, according to an exemplary, non-limiting embodiment of the present invention;

FIG. 5 is a plan view showing an air flow within an engine room of the vehicle, according to an exemplary, non-limiting embodiment of the present invention;

FIGS. 9A–9C are views showing a second exemplary, non-limiting modification of the present invention, similar to the view of FIG. 6;

DETAILED DESCRIPTION OF THE INVENTION

The exemplary, non-limiting embodiments of the present invention will be described below with reference to the accompanying drawings.

Figure 1:
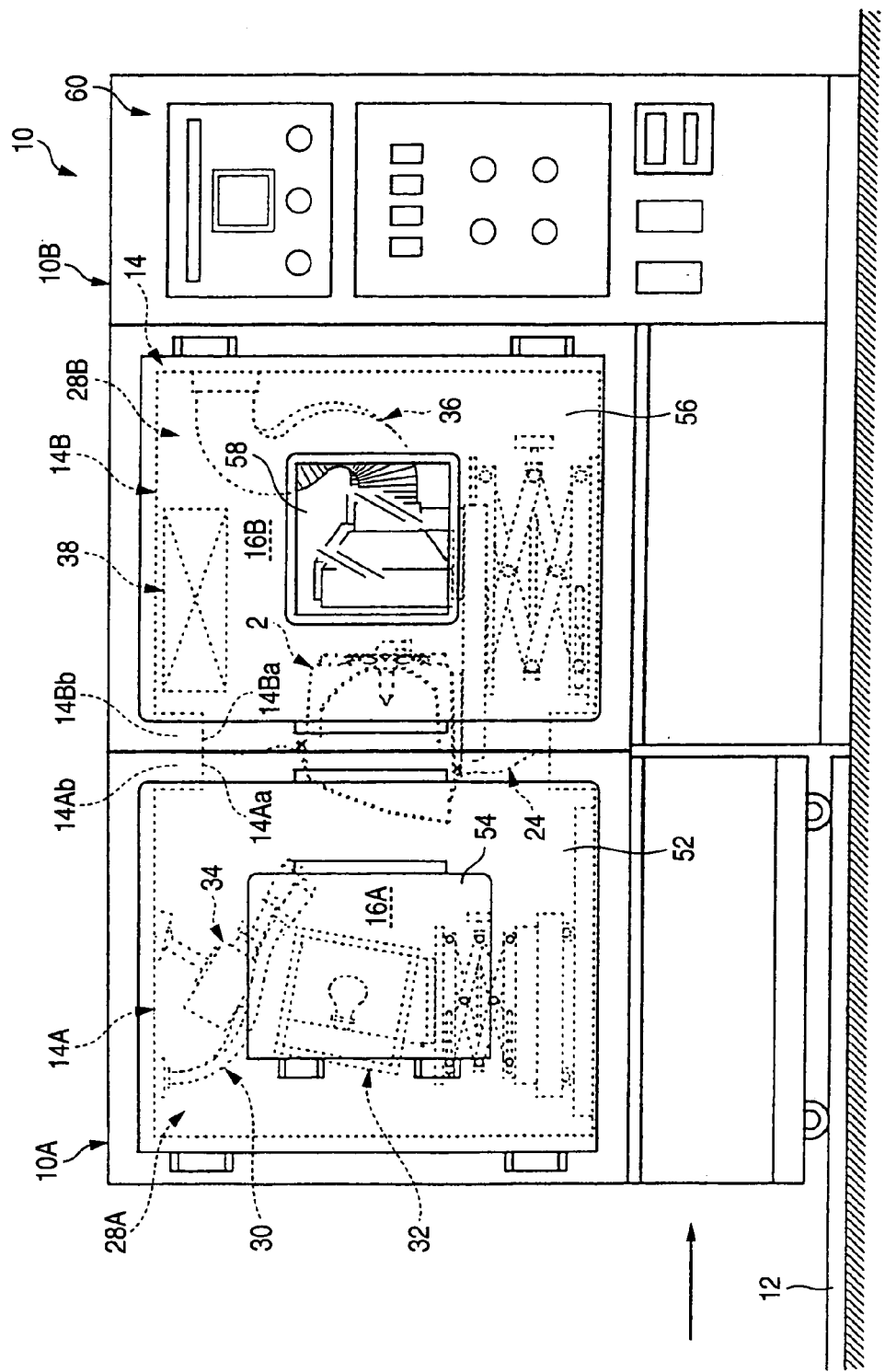
FIG. 1 is a side view showing the overall constitution of a water cloud evaluating device for vehicle lighting fixture, in a state of evaluation test, according to one exemplary, non-limiting embodiment of the present invention.
Figure 2:
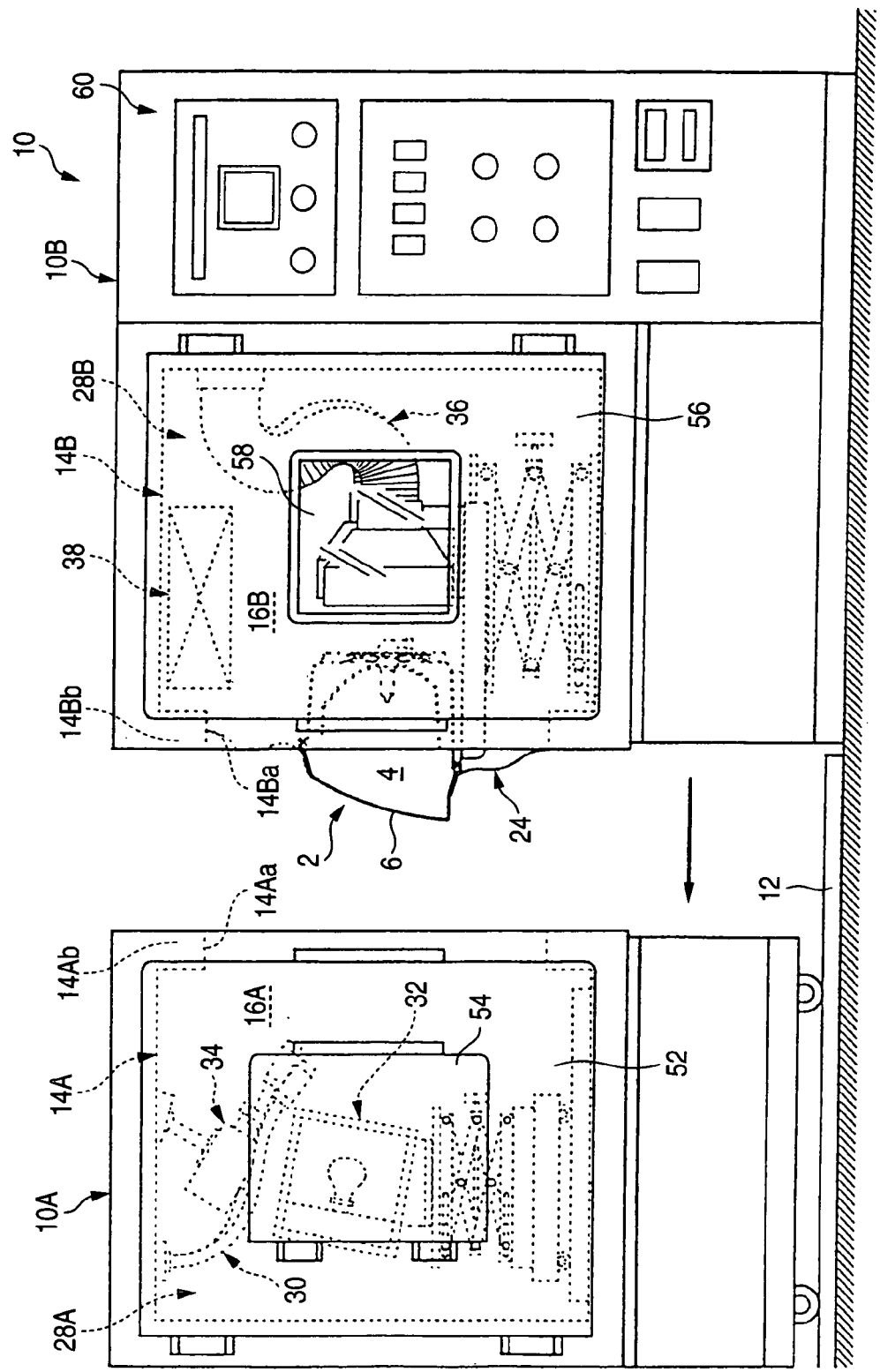
FIG. 2 is a side view showing the overall constitution of the water cloud evaluating device in a state other than evaluation test, according to an exemplary, non-limiting embodiment of the present invention.
Figure 3:
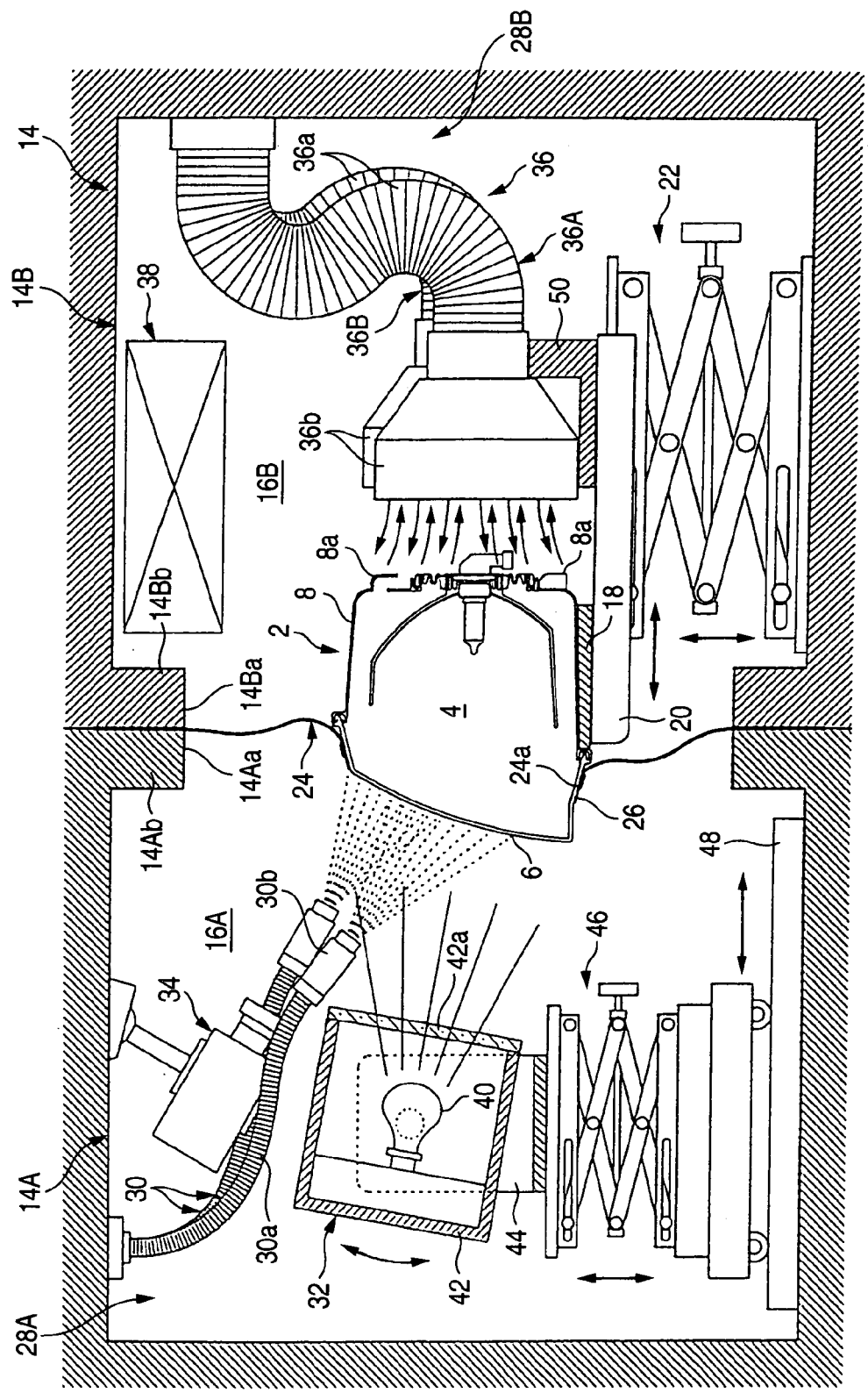
FIG. 3 is a side cross-sectional view of the essence of FIG. 1, according to an exemplary, non-limiting embodiment of the present invention.

FIGS. 1 and 2 are side views showing the overall constitution of a water cloud evaluating device 10 for a vehicle lighting fixture according to one exemplary, non-limiting embodiment of the invention in a state of evaluation test and a state other than evaluation test, respectively. FIGS. 3 and 4 are a side cross-sectional view and a plan cross-sectional view of the essence of FIG. 1, respectively.

In this water cloud evaluating device 10, the evaluation test is performed with the vehicle lighting fixture disposed to the left. Therefore, for the sake of convenience, the left direction is "forward" and the right direction is "backward" in the drawings.

As shown in FIGS. 1 and 2, the water cloud evaluating device 10 according to this exemplary, non-limiting embodiment evaluates the water cloud occurring within a lighting chamber 4 of the vehicle lighting fixture 2, and comprises a fixed portion 10B securely installed on the floor, and a movable portion 10A movable in the forward or backward direction along a rail 12 laid on the floor between a closed position (as indicated in FIG. 1) for closing the fixed portion 10B and an open position (as indicated in FIG. 2), that is apart from the fixed portion 10B.

This water cloud evaluating device 10 has a test vessel 14 composed of a first vessel 14A provided in the movable portion 10A and a second vessel 14B provided in the fixed portion 10B. A rear opening portion 14Aa of almost rectangular shape, longer transversely and opening rearward, is formed on a rear face wall 14Ab of the first vessel 14A, and a front opening portion 14Ba having the almost same shape as the opening portion 14Aa, opening forward, is formed on a front face wall 14Bb of the second vessel 14B. The vehicle lighting fixture 2 of evaluation object is disposed at a position on a mating face between the movable portion 10A and the fixed portion 10B within this test vessel 14.

As shown in FIGS. 3 and 4, the vehicle lighting fixture 2 of evaluation object in this exemplary, non-limiting embodiment is a head lamp, in which the lighting chamber 4 comprises a translucent cover 6 and a lamp body 8 being formed with plural vent holes 8a for communicating the lighting chamber 4 to a lighting fixture outer space. And this vehicle lighting fixture 2 is laid via a spacer 18 on a slider plate 20 to take the substantially same attitude as where it is mounted on an actual vehicle. This slider plate 20 is supported slidably in the forward and backward directions on the upper face of a ramp 22 having a pantograph laid on a lower face wall of the second vessel 14B. Thereby, the position of the vehicle lighting fixture 2 can be adjusted in the forward, backward, upper and lower directions.

The outer space of the vehicle lighting fixture 2 within the test vessel 14 is partitioned into a front space 16A and a rear space 16B near a joined face between the translucent cover 6 and the lamp body 8 by a partition member 24.

This partition member 24 is composed of an opaque sheet (e.g., a colored vinyl sheet) that can be easily cut by a knife or the like, and not transparent to visible light and near infrared rays. The partition member 24 is formed with an opening portion 24a having a shape corresponding to the outer circumferential shape of the translucent cover 6 in its central part. And this partition member 24 is secured to the translucent cover 6 on the circumferential portion of the opening portion 24a by an adhesive tape 26, as well as to a front face of the front face wall 14Bb of the second vessel 14B on its outer circumferential portion by the adhesive tape, thereby closing the front opening portion 14Ba of the second vessel 14B.

The water cloud evaluating device 10 according to this exemplary, non-limiting embodiment comprises vehicle outside environment simulation setting means 28A for simulatively setting the front space 16A in a predetermined vehicle outside environment and vehicle inside environment simulation setting means 28B for simulatively setting the rear space 16B in a predetermined vehicle inside environment. The first vessel 14A is provided with a water spray unit 30 and an illumination unit 32 as the simulation setting units comprising the vehicle outside environment simulation setting means 28A. On the other hand, the second vessel 14B is provided with an air flow generating unit 36 and a temperature/humidity control unit 38 as the simulation setting units comprising the vehicle inside environment simulation setting means 28B.

The water spray unit 30 sprays water to the translucent cover 6 and includes a universal pipe 30a extending from the upper face wall of the first vessel 14A and a nozzle 30b attached at its top end portion. Two units are provided at a predetermined spacing in the left and right direction. The universal pipe 30a can hold its shape in a deformable or deformed condition, thereby freely setting a piping passage. The nozzle 30b serves to spray the water supplied from water feeding means, not shown, through the universal pipe 30a.

In each water spray unit 30, the piping passage of the universal pipe 30 is adjusted manually or automatically, so that the nozzle 30b may be located forward and obliquely upward of the translucent cover 6 and directed to the translucent cover 6 at the time of an evaluation test. Also, in each water spray unit 30, the water spray amount from the nozzle 30b is regulated by water spray amount control means provided in the water feeding means. Moreover, the temperature of the water supplied to each water spray unit is controlled by water temperature control means provided in the water feeding means.

The illumination unit 32 applies infrared rays for heating the vehicle lighting fixture 2 to the translucent cover 6, and includes a plurality of infrared lamps 40 disposed in parallel to the left and right, a case 42 for accommodating the lamps 40, and a support bracket 44 for supporting the case 42 rotatably around the axial line. The case 42 has a translucent panel 42a with its rear face wall passing through. While four lamps 40 are provided in this exemplary, non-limiting embodiment of the present invention, the present invention is not limited thereto, and the number and type of lamps 40 may be varied and substituted with equivalents thereof, as would be understood by one of ordinary skill in the art.

This illumination unit 32 is laid on the upper face of a ramp 46 having the pantograph on the lower face of the support bracket 44. This ramp 46 is movable in the forward and backward direction along a rail 48 laid on a lower face wall of the first vessel 14A. Thereby, the illumination unit 32 allows easy adjustment for the illumination angles of the four infrared lamps 40 in the upper and lower direction, and the position in the upper and lower direction, and the forward and backward direction. Also, this illumination unit 32 has the illumination intensity and illumination time regulated by the control unit, not shown.

A monitor camera 34 is disposed to be able to photograph the translucent cover 6 while being positioned on an upper face wall of the first vessel 14A. The monitor camera 34 is connected to a monitor device and a recording device, both not shown. Thereby, an image photographed by the monitor camera is reflected on a screen of the monitor device to allow real time observation of an occurrence situation of the water cloud within the lighting chamber 4 of the vehicle lighting fixture 2. Also, the image photographed by the monitor camera 34 may be recorded on the recording device, as needed.

The air flow generating unit 36 comprises a blast duct 36A and a suction duct 36B disposed in parallel to the left and right. Each of the blast duct 36A and the suction duct 36B comprises a duct main body 36a extending from the rear face wall of the second vessel 14B, and a top end opening portion 36b attached to its top end portion. The duct main body 36a is made deformable, its piping passage being freely settable. The top end opening portion 36b has its opening shaped like a rectangle larger than the cross section of the duct main body 36a. And the blast duct 36A and the suction duct 36B are laid via a support block 50 on the slider plate 20 so that its top end opening portion 36b may be opened in the horizontal direction.

The blast duct 36A is disposed near an outer end portion of the vehicle lighting fixture 2 in the vehicle width direction to be open to the fore, and blasts the air to the lamp body 8 by a blast pump, not shown. On the other hand, the suction duct 36B is provided near an inner end portion of the vehicle lighting fixture 2 in the vehicle width direction to be open to the fore, and sucks the air within the second vessel 14B by a suction pump, not shown. And the blast duct 36A and the suction duct 36B produce the air flow along the lamp body 8.

Referring to FIG. 5, the reason why the air flow is produced will be discussed below.

FIG. 5 is a plan view showing a behavior of the air flow within an engine room 102 of the vehicle 100.

As shown in FIG. 5, a running wind flows via a front grille 104 and a radiator grille 106 into an engine room 102, as indicated by the arrow A, while the vehicle is running. Also, outside air is compulsorily sucked in by driving a radiator fan, and flows into the engine room 102 as indicated by the arrow A, if the engine 108 is rotating, while the vehicle is stopped. The inflow air flows backward along the engine 108 within the engine room 102, as indicated by the arrow B, and makes contact with a dash panel 110 to be bent to the left and right, as indicated by the arrow C, and passed forward along a fender panel 112. The air flow contacts an outer end portion of the lamp body 8 in the vehicle width direction for the vehicle lighting fixture 2 from the rear side, as indicated by the arrow D, and flows toward an inner end portion in the vehicle width direction along the lamp body 8 as indicated by the arrow E to join the flow as indicated by the arrow B.

Thus, in this exemplary, non-limiting embodiment, the air flow similar to the air flow along the lamp body 8 occurring within the engine room 102 in this way is generated within the blast duct 36A and the suction duct 36B.

A constant temperature and humidity control unit 38 controls the temperature and humidity of the rear space 16B by control means, not shown, and thereby enables the second vessel 14B to operate as a thermo-hygrostat. This constant temperature and humidity control unit 38 is attached on an upper face wall of the second vessel 14B, and sets the rear space 16B at the substantially same temperature and humidity as the measured temperature and humidity within the engine room of the actual vehicle.

As shown in FIGS. 1 and 2, the first vessel 14A is openable or closable from the side by a hinged large door 52, which is provided with a hinged small door 54. And the water spray unit 30 and the illumination unit 32 are easily installed by adjusting the positions, owing to the existence of the large door 52 and the small door 54. On the other hand, the second vessel 14B is openable or closable from the side by a hinged large door 56, which is provided with a view area 58. And the air flow generating unit 36 has the position easily adjusted, and allows confirmation for the inside of the second vessel 14B during the evaluation test, owing to the existence of the large door 56 and the view area 58.

A control board 60 is provided adjacently to the second vessel 14B in the fixed portion 10B of the water cloud evaluating device 10. This control board 60 is equipped with control means and operation switches for controlling the vehicle outside environment simulation setting means 28A and the vehicle inside environment simulation setting means 28B.

Figure 6A:
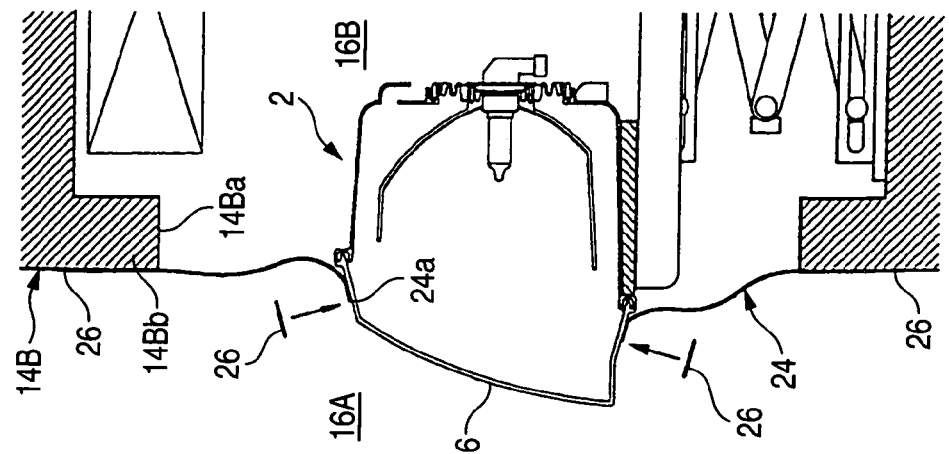
FIGS. 6A–6C are views showing away of mounting a partition member for the water cloud evaluating device, like the view of FIG. 3, according to an exemplary, non-limiting embodiment of the present invention.
Figure 6B:
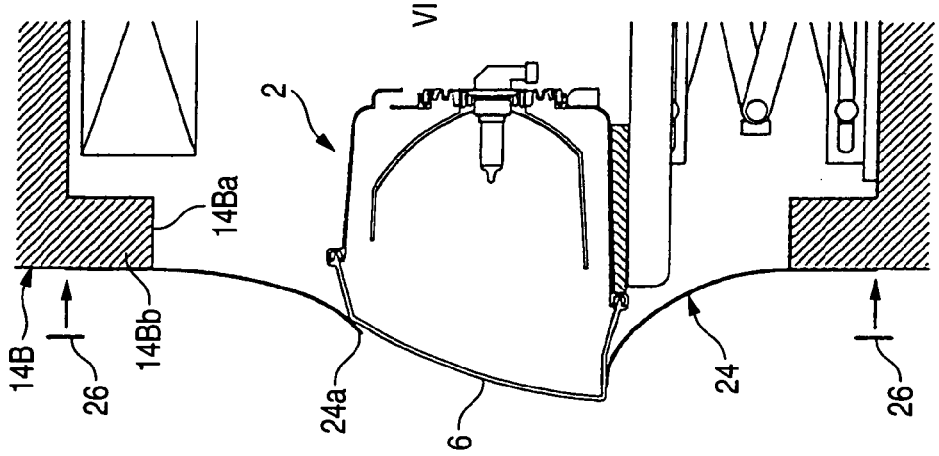
Figure 6C:
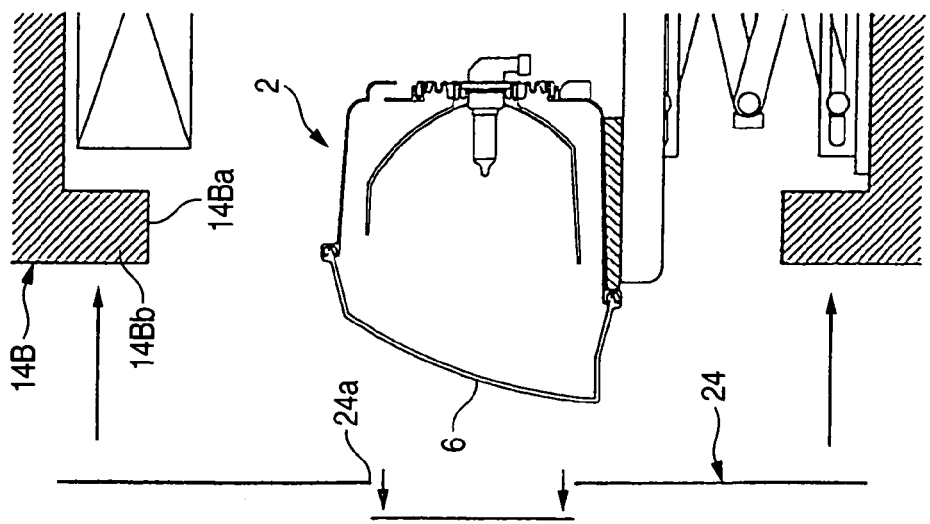
Figure 7:
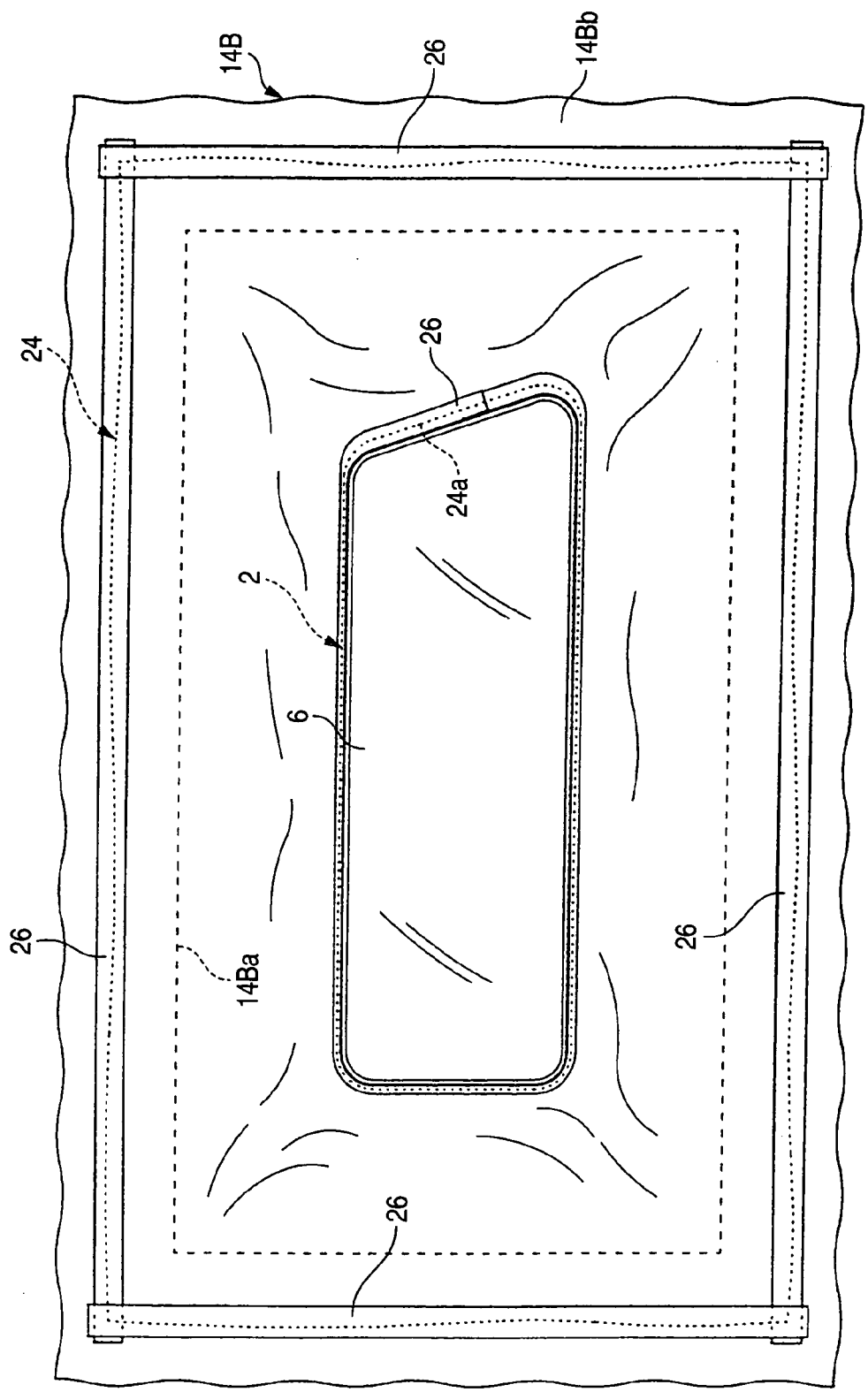
FIG. 7 is a perspective view as seen from the arrow VII in FIG. 6, according to an exemplary, non-limiting embodiment of the present invention.

FIGS. 6A–6C illustrate how the partition member 24 is mounted, like the view of FIG. 3, and FIG. 7 is a perspective view of FIG. 6, as seen from the arrow VII.

First, a sheet having a slightly larger size than the front opening portion 14Ba of the second vessel 14B is prepared, and the opening portion 24a is formed by cutting out a central portion of the sheet, using a knife or the like, thereby producing the sheet 24, as shown in FIG. 6A. In this case, the opening portion 24a is formed slightly smaller than the outer circumferential shape of the translucent cover 6 for the vehicle lighting fixture 2.

As shown in FIG. 6B, while this sheet 2 is pressed against the front face wall 14Bb of the second vessel 14B from the fore side, an outer circumferential portion of the sheet 24 is fixed to the front face of the front face wall 14Bb for the second vessel 14B by an adhesive tape 26. At this time, the fixed position of the sheet 24 is adjusted so that the opening portion 24a may be located on the translucent cover 6.

Thereafter, the sheet 24 is fixed to the translucent cover 6 on the circumferential portion of the opening portion 24a by the adhesive tape 26 in a state where the circumferential portion of the opening portion 24a in the sheet 24 is pressed against the outer circumferential portion of the translucent cover 6, as shown in FIG. 6C and FIG. 7. Thereby, the sheet 24 is completed as the partition member 24 for partitioning the outer space of the vehicle lighting fixture 2 into the front space 16A and the rear space 16B.

As described above in detail, the water cloud evaluating device 10 according to this exemplary, non-limiting embodiment comprises the partition member 24 for partitioning the outer space of the vehicle lighting fixture 2 into the front space 16A and the rear space 16B around the outer circumferential portion of the lighting fixture, vehicle outside environment simulation setting means 28A for simulatively setting the front space 16A in a predetermined vehicle outside environment, and vehicle inside environment simulation setting means 28B for simulatively setting the rear space 16B in a predetermined vehicle inside environment.

Therefore, the water cloud evaluation is made in the artificial environment of the lighting fixture outer space close to the state where the vehicle lighting fixture is mounted on the actual vehicle, although the vehicle lighting fixture is not mounted on the actual vehicle, whereby the water cloud evaluation results are obtained at high precision. Further, the water cloud evaluation is made by the bench test as described above, and can be repeated many times in a short time to reduce the cost.

In this case, the front space 16A is provided with a water spray unit 30 and an illumination unit 32 as the simulation setting units comprising the vehicle outside environment simulation setting means 28A, whereby the translucent cover 6 undergoes the water spray and the infrared radiation. Therefore, it is possible to produce a vehicle outside environment very close to the state where the lighting fixture is mounted on the actual machine in consideration of the rainfall, car washing or insolation, whereby the water cloud evaluation is made at a higher precision.

Also, the rear space 16B is provided with an air flow generating unit 36 and a temperature/humidity control unit 38 as the simulation setting units comprising the vehicle inside environment simulation setting means 28B. Therefore, it is possible to make the environment of the rear space 16B substantially close to the environment within the engine room, whereby the water cloud evaluation for the vehicle lighting fixture 2 has a substantially higher precision. Further, the air flow generating unit 36 generates an air flow inward in the vehicle width direction along the lamp body 8 by the blast duct 36A and the suction duct 36B, so that the air flow near the lamp body 8 becomes close to that on the actual vehicle. As a result, the water cloud evaluation has higher precision.

Moreover, in this exemplary, non-limiting embodiment, the partition member 24 is formed with the opening portion 24a in the sheet that is easily cuttable by the knife or the like, bringing about the following operation effect.

A part of the sheet is cut out by the knife or the like to form the opening portion 24a corresponding to the vehicle lighting fixture 2 to be evaluated, whereby the partition member 24 is easily produced for the vehicle lighting fixture with the outer circumferential portion of the lighting fixture having different shape or size. In this case, the sheet having flexibility is easily disposed according to the shape of the outer circumferential portion of the lighting fixture. Also, the sheet which is easily cuttable by the knife or the like is generally quite cheaper than the related art rigid plate. Thus, the partition member 24 has a substantially lower manufacturing cost.

Since the partition member 24 is fixed to the translucent cover 6 for the vehicle lighting fixture 2 on the circumferential portion of the opening portion 24a by the adhesive tape 26, the outer space of the vehicle lighting fixture 2 is fully partitioned into the front space 16A and the rear space 16B. Thereby, the water cloud evaluation results are obtained at a higher precision.

Also, in this exemplary, non-limiting embodiment, since the partition member 24 is formed of an opaque member to the visible and near infrared radiation, it is possible to effectively suppress the influence of radiant heat from the illumination unit 32 on the temperature of the rear space 16B.

In this exemplary, non-limiting embodiment, when the partition member 24 is produced, one or more short slits may be formed around the opening portion 24a in the sheet formed with the opening portion 24a. In this way, even when the vehicle lighting fixture 2 to be evaluated has a complex shape, the shape of the opening portion 24a is easily adapted to the shape of the outer circumferential portion of the lighting fixture.

Instead of the partition member 24 composed of the easily cuttable sheet opaque to visible and near infrared radiation, the partition member may be composed of other sheets or a rigid sheet.

In this exemplary, non-limiting embodiment, since the water spray unit 30, the illumination unit 32 and the air flow generating unit 36 are configured to be movable, the following operation effect is obtained.

The water spray unit 30 and the illumination unit 32 are appropriately moved to adjust their position and/or attitude, whereby the front space 16A is easily set in the desired vehicle outside environment by simulation. Also, the air flow generating unit 36 is appropriately moved to adjust its position or attitude, whereby the rear space 16B is easily set in the desired vehicle outside environment by simulation. Thereby, the water cloud evaluation results are obtained at a higher precision.

Also, in installing or removing the vehicle lighting fixture 2 to be evaluated, the water spray unit 30, the illumination unit 32 and the air flow generating unit 36, which are movable, are appropriately moved. Thus, the installation or removal operation is facilitated.

In this exemplary, non-limiting embodiment, the water spray unit 30 and the illumination unit 32 comprising the vehicle outside environment simulation setting means 28A are disposed within the first vessel 14A formed with the rear opening portion 14Aa that opens to the rear, and are less affected by external disturbance than disposed in open space. The vehicle outside environment is thus more easily set by simulation.

Also, the air flow generating unit 36 and the temperature/humidity control unit 38 comprising the vehicle inside environment simulation setting means 28B are disposed within the second vessel 14B formed with the front opening portion 14Ba that opens to the fore, and is less affected by external disturbance than disposed in open space, whereby the vehicle inside environment is more easily set by simulation.

Also, in this exemplary, non-limiting embodiment, since the partition member 24 is provided to enclose the front opening portion 14Ba of the second vessel 14B, the rear space 16B is a substantially sealed space, whereby the vehicle inside environment is more easily set by simulation.

Further, in this exemplary, non-limiting embodiment, the first vessel 14A is movable between a position for closing the rear opening portion 14Aa and the front opening portion 14Ba of the second vessel 14B and a position for opening them, whereby the front space 16A and the rear space 16B are made the sealed space at the closed position. Therefore, it is possible to more easily set not only the vehicle inside environment but also the vehicle outside environment by simulation. Also, if the first vessel 14A is configured to be movable, the water spray unit 30 and the illumination unit 32 comprising the vehicle outside environment simulation setting means 28A can be moved substantially simultaneously, thereby facilitating the operation of installing or removing the vehicle lighting fixture 2. When the first vessel 14A is configured to be movable, the water cloud occurrence state within the lighting chamber 4 is easily observed through the eyes at the position near the translucent cover 6 after the evaluation test, whereby the water cloud evaluation is made at a higher precision.

Though in the above exemplary, non-limiting embodiment, the first vessel 14A is movable, the second vessel 14B may be movable, or both the first vessel 14A and the second vessel 14B may be movable, thereby bringing about the substantially same operation effect of the above exemplary, non-limiting embodiment.

Though in the above exemplary, non-limiting embodiment, the front space 16A and the rear space 16B of the partition member 24 are made the sealed space by the first vessel 14A and the second vessel 14B, one or both of the front space 16A and the rear space 16B may be made open.

It is also possible to take other constitutions in which plural simulation setting units comprising the vehicle outside environment simulation setting means 28A and the vehicle inside environment simulation setting means 28B are all fixed.

Modifications of the foregoing exemplary, non-limiting embodiments will be described below.

FIG. 8 is a view showing a first modified exemplary, non-limiting embodiment of the above embodiment, like the view of FIG. 6.

In this modified exemplary, non-limiting embodiment, a partition member 62 formed with an opening portion 62a in a flexible sheet is employed, instead of the partition member 24 formed with the opening portion 24a in the sheet that is easily cuttable by the knife or the like as in the above exemplary, non-limiting embodiment. This partition member 62 is also formed from an opaque member (e.g., black rubber sheet) to the visible or near infrared radiation. The constitution is the same as in the above exemplary, non-limiting embodiment, except for the partition member 62.

Mounting the partition member 62 according to the modified exemplary, non-limiting embodiment is performed in the following way.

Figure 8A:
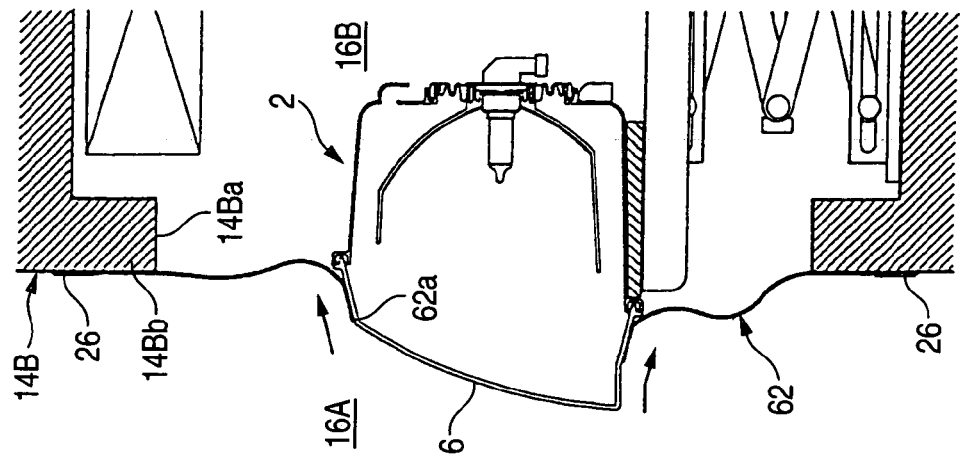
FIGS. 8A–8C are views showing a first exemplary, non-limiting modification of the present invention, similar to the view of FIG. 6.

First, the sheet 62 having a slightly larger size than the front opening portion 14Ba of the second vessel 14B, with the opening portion 62a formed in the central portion, is pressed against the front face wall 14Bb of the second vessel 14B from the fore side, as shown in FIG. 8A. This opening portion 62a is formed in an appropriate size smaller than the opening portion 24a of the partition member 24 in the above exemplary, non-limiting embodiment.

Figure 8B:
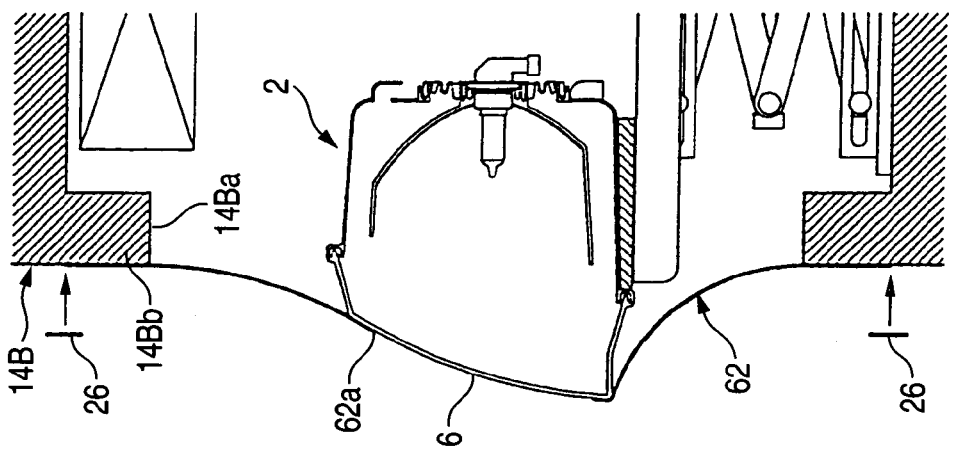

Then, the outer circumferential portion of the sheet 62 is fixed to the front face of the front face wall 14Bb in the second vessel 14B by the adhesive tape 26, as shown in FIG. 8B. At this time, the fixed position of the sheet 62 is adjusted so that the opening portion 62a is located on the translucent cover 6 in the same way as in the above exemplary, non-limiting embodiment. However, because the sheet 62 is flexible, the circumferential portion of the opening portion 62a is intimately contacted with the translucent cover 6.

Figure 8C:
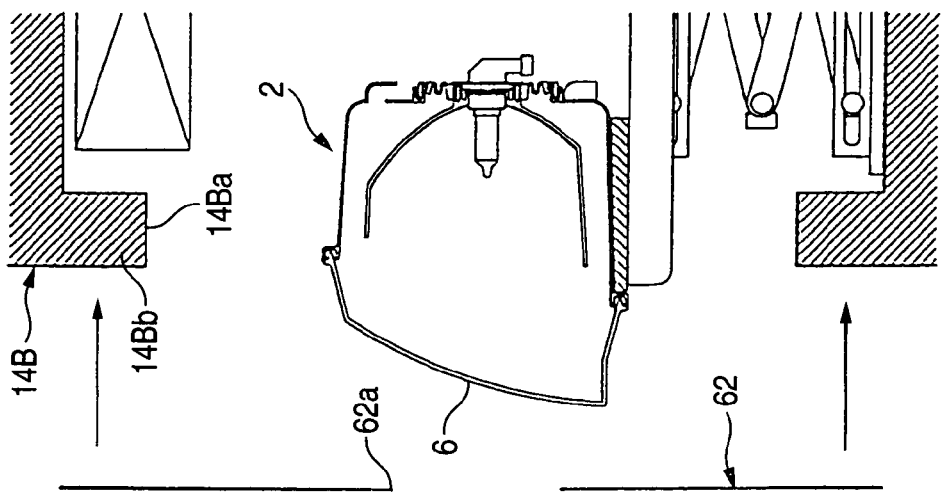

Thereafter, the circumferential portion of the opening portion 62a in the sheet 62 is moved back along the outer circumference of the translucent cover 6 while being elastically deformed, and fitted over the translucent cover 6, as shown in FIG. 8C. Thereby, the sheet 62 is completed as the partition member 62 for partitioning the outer space of the vehicle lighting fixture into the front space 16A and the rear space 16B.

In this first modified exemplary, non-limiting embodiment, the partition member 62 formed with the predetermined opening portion 62a in the flexible sheet is employed, bringing about the following operation effect.

The circumferential portion of the opening portion 62a in the sheet 62 is fitted over the outer circumferential portion of lighting fixture for the vehicle lighting fixture 2, while being elastically deformed. Thus, the partition member 62 is easily formed.

In this case, for the vehicle lighting fixture in which the outer circumferential portion of lighting fixture has a different shape or size, the same sheet 62 can be appropriated to form the partition member 62 in a range where the sheet 62 is elastically deformed, whereby there is no or less need for producing the new partition member, thus greatly reducing the manufacturing cost of the partition member 62.

When the constitution of the modified exemplary, non-limiting embodiment is employed, the partition member 62 may be fixed to the outer circumferential portion of the translucent cover 6 around the opening portion 62a by the adhesive tape to make more perfect the functions of the partition member.

FIG. 9 is a view showing a second modified exemplary, non-limiting embodiment of the foregoing embodiments, like the view of FIG. 6.

In this exemplary, non-limiting embodiment, a partition member 64 includes a sheet 66 and a rigid plate 68 for supporting the circumferential portion of the sheet 66. The constitution is the same as in the above exemplary, non-limiting embodiment, except for this partition member 64.

The sheet 66, like the sheet 24 in the above exemplary, non-limiting embodiment, is an opaque sheet (e.g., colored vinyl sheet) to visible and near infrared radiation, which is easily cuttable by the knife or the like, and formed with an opening portion 66a having the shape corresponding to the outer circumferential shape of the translucent cover 6 in its central portion.

The rigid plate 68 is metallic, and formed with an opening portion 68a having a larger size than the vehicle lighting fixture 2 in its central portion, and a flange portion 68b extending backward on its outer circumferential portion. And the flange portion 68b of the rigid plate 68 is fixed to an inner circumferential end face of the front face wall 14Bb for the second vessel 14B by plural bolts.

Mounting the partition member 64 according to the modified exemplary, non-limiting embodiment is performed in the following way.

First, the rigid plate 68 is fixed to the inner circumferential end face of the front face wall 14B for the second vessel 14B by the plural bolts 70, as shown in FIG. 9A. On the other hand, a sheet having a slightly larger size than the opening portion 68a of the rigid plate 68 is prepared, and a central portion of the sheet is cut out by the knife or the like to form the opening portion 66a, whereby the sheet 66 is produced. In this case, the opening portion 66a is set in the almost same size as the opening portion 24a of the partition member 24 in the above exemplary, non-limiting embodiment.

And while this sheet 66 is pressed against the front face of the rigid plate 68, and an outer circumferential portion of the sheet 66 is fixed to the front face of the rigid plate 68 by the adhesive tape 26, as shown in FIG. 9B. At this time, the fixed position of the sheet 66 is adjusted so that the opening portion 66a may be located on the translucent cover 6 in the same way as in the above exemplary, non-limiting embodiment.

Thereafter, the sheet 66 is fixed to the translucent cover 6 around the opening portion 66a by the adhesive tape 26 in a state where the circumferential portion of the opening portion 66a in the sheet 66 is pressed against the outer circumferential portion of the translucent cover 6, as shown in FIG. 9C. Thus, the partition member 64 for partitioning the outer space of the vehicle lighting fixture 2 into the front space 16A and the rear space 16B is completed.

Employing the constitution of this modified exemplary, non-limiting embodiment, the following operation effect, as well as the same operation effect as in the above exemplary, non-limiting embodiment, are obtained.

That is, the partition member 64 is composed of the sheet 66 and the rigid plate 68 for supporting its circumferential portion, but is not composed of the sheet 24 alone as in the above exemplary, non-limiting embodiment. As a result, the sheet 66 is reduced in size, and a reduced amount of material is used. Also, since the rigid plate 68 is appropriated for the vehicle lighting fixture in which the outer circumferential portion of the lighting fixture has different shape or size, it is only necessary to replace the sheet 66 of smaller size, when the evaluation test is made for the new vehicle lighting fixture. Thereby, the water cloud evaluation is made at a lower cost.

Though in the modified exemplary, non-limiting embodiments, the rigid plate 68 is metallic, the rigid plate 68 may be made of other materials including (but not limited to) synthetic resin.

Figure 10:
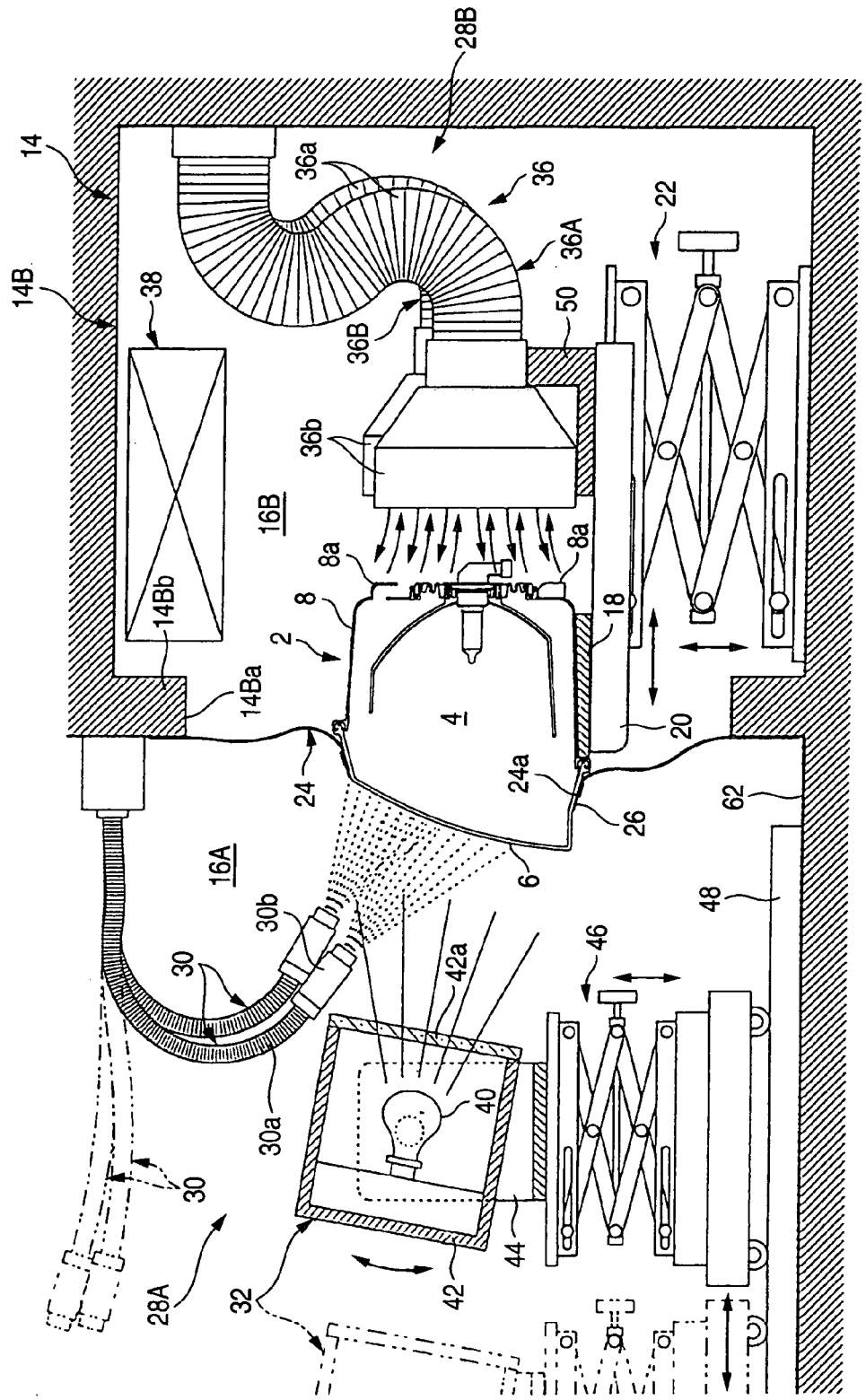
FIG. 10 is a view showing a fourth, exemplary, non-limiting modification of the present invention, similar to the view of FIG. 3.

FIG. 10 is a view showing a third modified exemplary, non-limiting embodiment of the above embodiment, like the view of FIG. 3. In FIG. 10, the front space 16A is the open space, and the rear space 16B is the sealed space by the second vessel 14B.

In this third modified exemplary, non-limiting embodiment, a floor face 62 extends forward to be almost flush with a lower face wall of the second vessel 14B in the front of the second vessel 14B. Additionally, the universal pipe 30a of each water spray unit 30 extends from the front face of the front face wall 14Bb for the second vessel 14B, and the illumination unit 32 is laid on an upper plane of the ramp 46 to be movable along a rail 48 laid on the floor face 62. In this case, the rail 48 in the modified exemplary, non-limiting embodiment extends forward a little longer to allow the illumination unit 32 to be more substantially moved in the back and forth direction.

In this third modified exemplary, non-limiting embodiment, the vehicle inside environment simulation setting means 28B has exactly the same constitution as in the above exemplary, non-limiting embodiment.

Employing the constitution of the third modified exemplary, non-limiting embodiment, the water cloud evaluating device has the simplified constitution.

In this third modified exemplary, non-limiting embodiment, the water spray unit 30 and the illumination unit 32, which are configured to be movable as the simulation setting units comprising the vehicle outside environment simulation setting means 28A, are appropriately moved to adjust the position and/or attitude, so that the front space 16A is easily set in the desired vehicle outside environment by simulation. Also, in installing or removing the vehicle lighting fixture 2 to be evaluated, the water spray unit 30 and the illumination unit 32 may be moved to the positions as indicated by the two-dot chain line in FIG. 10, thereby facilitating the installation or removal operation.

Figure 11:
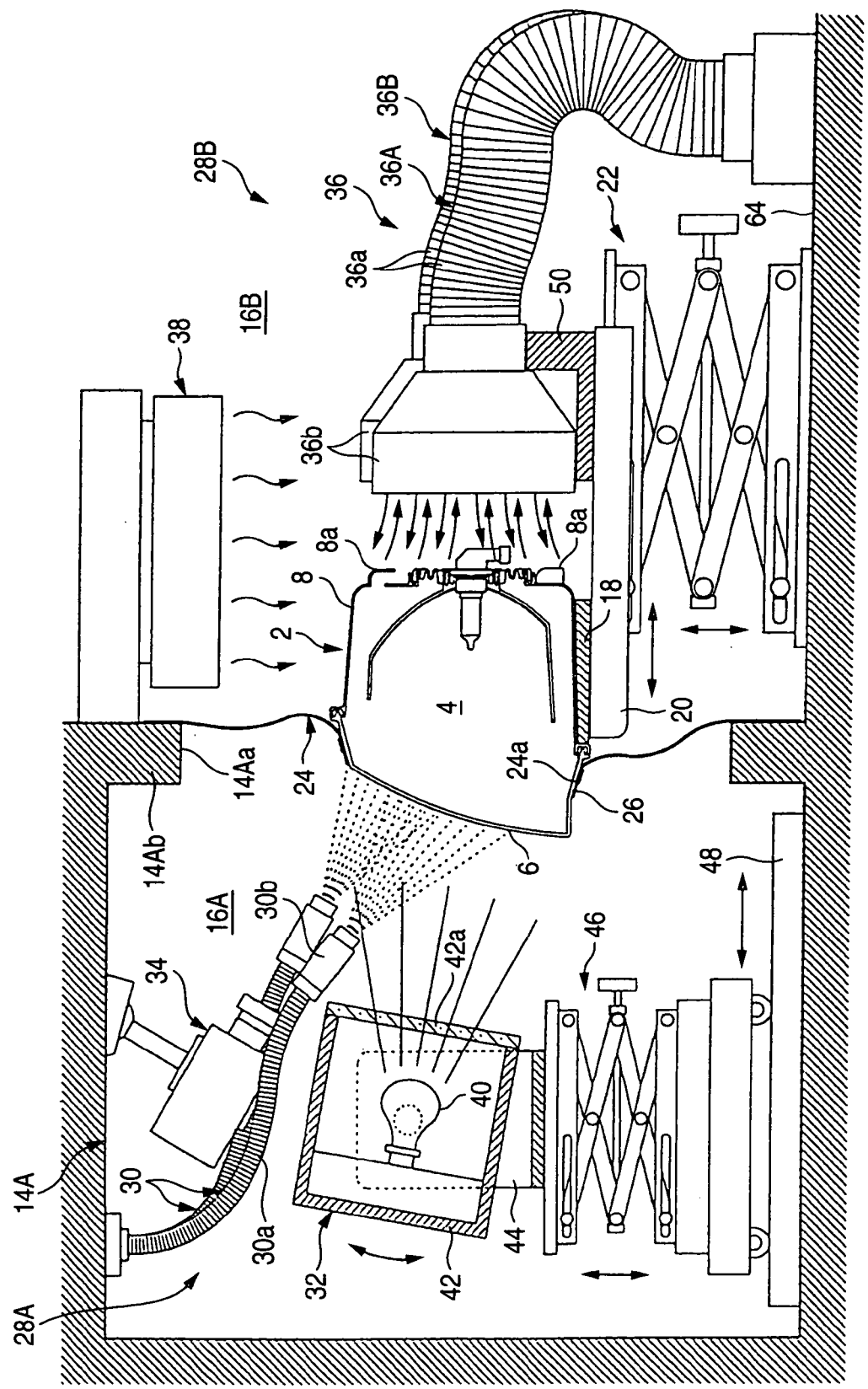
FIG. 11 a view showing a fifth, exemplary, non-limiting modification of the present invention, similar to the view of FIG. 3.

FIG. 11 is a view showing a fourth modified exemplary, non-limiting embodiment of the above embodiment, like the view of FIG. 3. In FIG. 11, the front space 16A is the sealed space by the first vessel 14A, and the rear space 16B is the open space.

In this fourth modified exemplary, non-limiting embodiment, a floor face 64 extends backward to be almost flush with a lower face wall of the first vessel 14A in the rear of the first vessel 14A. Further, the air flow generating unit 36 extends from the floor face 64, and the ramp 22 is laid on the floor face 64. Additionally, the temperature/humidity control unit 38 is mounted on the rear face wall 14Ab of the first vessel 14A. Moreover, in this modified exemplary, non-limiting embodiment, the partition member 24 is fixed to the rear face wall 14Ab of the first vessel 14A on its outer circumferential portion by the adhesive tape.

In this modified exemplary, non-limiting embodiment, the vehicle outside environment simulation setting means 28A has exactly the same constitution as in the above exemplary, non-limiting embodiment.

Employing the constitution of the modified exemplary, non-limiting embodiment, the water cloud evaluating device has the simplified constitution.

In this modified exemplary, non-limiting embodiment, since the air flow generating unit 36 is movable as the simulation setting unit comprising the vehicle inside environment simulation setting means 28B, the blast duct 36A and the suction duct 36B making up this air flow generating unit 36 are appropriately moved to adjust its position or attitude, whereby the rear space 16B is easily set in the desired vehicle inside environment by simulation. Also, in installing or removing the vehicle lighting fixture 2 to be evaluated, the air flow generating unit 36 may be appropriately moved, thereby facilitating the installation or removal operation.

Figure 12:
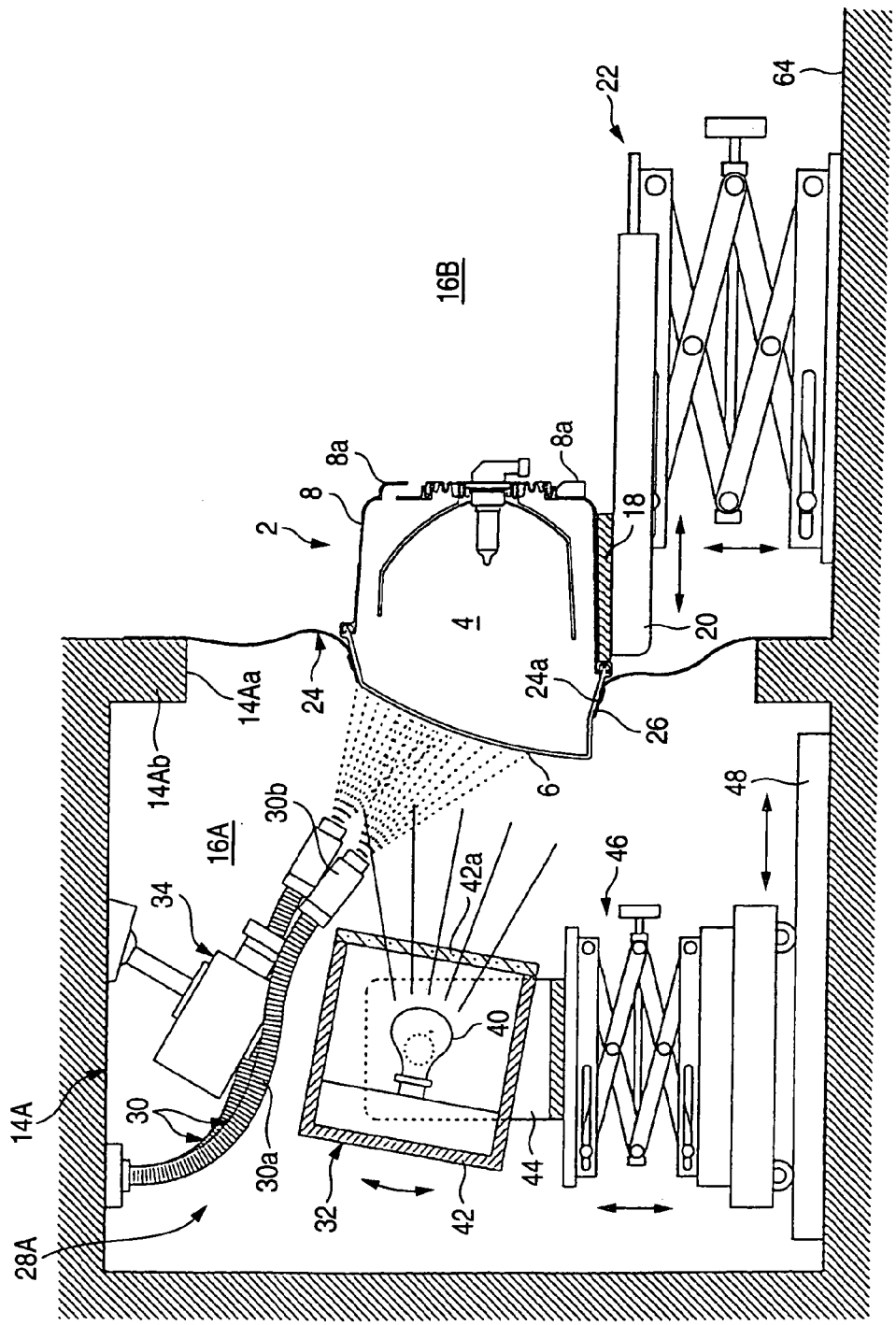
FIG. 12 a view showing a sixth, exemplary, non-limiting modification of the present invention, similar to the view of FIG. 3.

FIG. 12 is a view showing a fifth modified exemplary, non-limiting embodiment of the above embodiment, like the view of FIG. 3. In FIG. 12, the front space 16A is the sealed space by the first vessel 14A, and the rear space 16B is the open space, in which the vehicle outside environment simulation setting means 28A is only provided.

In this fifth modified exemplary, non-limiting embodiment, like the second modified exemplary, non-limiting embodiment, the floor face 64 extends backward to be almost flush with the lower face wall of the first vessel 14A in the rear of the first vessel 14A, and the ramp 22 is laid on the floor face 64. Also, the partition member 24 is fixed to the rear face of the rear face wall 14Ab in the first vessel 14A on its outer circumferential portion by the adhesive tape.

In this fifth modified exemplary, non-limiting embodiment, assuming the vehicle inside environment is in an ordinary temperature windless condition, the evaluation for water cloud caused by a change in the vehicle outside environment is simply made. That is, the vehicle inside environment simulation setting means 28B as in the second modified exemplary, non-limiting embodiment is not provided, and accordingly the air flow generating unit 36 and the temperature/humidity control unit 38 are not provided.

In this fifth modified exemplary, non-limiting embodiment, the vehicle outside environment simulation setting means 28A has exactly the same constitution as in the above embodiment.

The present invention has various advantages. For example, but not by way of limitation, employing the constitution of the modified exemplary, non-limiting embodiment, the water cloud evaluating device has the simplified constitution.

Particularly, since the air flow generating unit 36 and the temperature/humidity control unit 38 are not provided in this modified exemplary, non-limiting embodiment, the operation of installing or removing the vehicle lighting fixture 2 to be evaluated is quite easily performed. Accordingly, the evaluation for water cloud caused by a change in the vehicle outside environment is efficiently made for plural vehicle lighting fixtures.

In the above exemplary, non-limiting embodiment and the modified embodiments, the vehicle lighting fixture 2 to be evaluated for water cloud is a head lamp. However, when the water cloud evaluation is subjected to an auxiliary head lamp such as a fog lamp or a marker lamp such as a front turn signal lamp or a rear combination lamp, it is possible to achieve the same operation effects of the above exemplary, non-limiting embodiment and the modified embodiments by employing the same constitution of the above exemplary, non-limiting embodiment and the modified embodiments.

The present invention is not limited to the specific above-described embodiments. It is contemplated that numerous modifications may be made to the present invention without departing from the spirit and scope of the invention as defined in the following claims.

What is claimed is:

1. A device for evaluating a water cloud occurring within a lighting chamber of a vehicle lighting fixture, said lighting chamber including a translucent cover and a lamp body formed with vent holes for communicating with an outer space of said lighting chamber, said device comprising:
   a support that supports the vehicle lighting fixture within the device;
   a partition member partitioning said outer space of said lighting fixture into a front space and a rear space around an outer circumferential portion of said lighting fixture, wherein the partition member is independent of the support;
   vehicle outside environment simulation setting means for simulatively setting said front space in a vehicle outside environment; and vehicle inside environment simulation setting means for simulatively setting said rear space in a vehicle inside environment, wherein said partition member has a predetermined opening portion formed in a cuttable sheet.

2. The device according to claim 1, wherein said partition member comprises said cuttable sheet and a rigid plate for supporting the circumferential portion of said sheet.

3. The device according to claim 1, wherein said partition member comprises a member that is substantially opaque to visible and near infrared radiation.

4. A device for evaluating a water cloud occurring within a lighting chamber of a vehicle lighting fixture, said lighting chamber including a translucent cover and a lamp body formed with vent holes for communicating with an outer space of said lighting fixture, said device comprising:

a support that supports the vehicle lighting fixture within the device;

a partition member partitioning said outer space of said lighting fixture into a front space and a rear space around an outer circumferential portion of said lighting fixture, wherein the partition member is independent of the support;

vehicle outside environment simulation setting means for simulatively setting said front space in a vehicle outside environment; and vehicle inside environment simulation setting means for simulatively setting said rear space in a vehicle inside environment, wherein said partition member has a predetermined opening portion formed in a flexible sheet.

5. The device according to claim 4, wherein said partition member comprises said flexible sheet and a rigid plate for supporting the circumferential portion of said sheet.

6. The device according to claim 4, wherein said partition member comprises a member that is substantially opaque to visible and near infrared radiation.

7. A device for evaluating a water cloud occurring within a lighting chamber of a vehicle lighting fixture, said lighting chamber including a translucent cover and a lamp body formed with vent holes for communicating with an outer space of said lighting fixture, said device comprising:

a partition member partitioning said outer space of said lighting fixture into a front space and a rear space around the outer circumferential portion of said lighting fixture;

vehicle outside environment simulation setting means for simulatively setting said front space in a vehicle outside environment; and vehicle inside environment simulation setting means for simulatively setting said rear space in a vehicle inside environment, wherein said vehicle outside environment simulation setting means comprises at least one simulation setting unit provided in said front space, and said vehicle inside environment simulation setting means comprises at least one simulation setting unit provided in said rear space, and wherein at least one of said at least one simulation setting unit in said front space and said at least one simulation setting unit in said second space is movable.

8. The device according to claim 7, wherein each said at least one simulation setting unit that comprises said vehicle outside environment simulation setting means is disposed in a first vessel formed with a portion that opens to a rear direction.

9. The device according to claim 8, wherein said partition member encloses said opening in said first vessel.

10. The device according to claim 8, wherein said first vessel is movable between a position for opening and closing the opening in said first vessel.

11. The device according to claim 7, wherein each said at least one simulation setting unit that comprises said vehicle inside environment simulation setting means is disposed in a second vessel formed with a portion that opens to a fore direction.

12. The device according to claim 11, wherein said partition member encloses said opening in said second vessel.

13. The device according to claim 11, wherein said second vessel is movable between a position for opening and closing the opening in said second vessel.

14. A device for evaluating a water cloud occurring within a lighting chamber of a vehicle lighting fixture, said lighting chamber including a translucent cover and a lamp body formed with vent holes for communicating with an outer space of said lighting chamber, said device comprising:

a partition member partitioning said outer space of said lighting fixture into a front space and a rear space around the outer circumferential portion of said lighting fixture;

vehicle outside environment simulation setting means for simulatively setting said front space in a vehicle outside environment; and vehicle inside environment simulation setting means for simulatively setting said rear space in a vehicle inside environment, wherein said vehicle outside environment simulation setting means comprises at least one simulation setting unit provided in said front space, and said vehicle inside environment simulation setting means comprises at least one simulation setting unit provided in said rear space, wherein each said at least one simulation setting unit that comprises said vehicle outside environment simulation setting means is disposed within a first vessel formed with a rear opening portion that opens to a rear direction, and each said at least one simulation setting unit that comprises said vehicle inside environment simulation setting means is disposed within a second vessel formed with a front opening portion that opens to the front, wherein said partition member is provided to enclose one of the rear opening portion in said first vessel and the front opening portion in said second vessel, and wherein at least one of said first vessel and said second vessel is movable between a position for closing the rear opening portion in said first vessel and the front opening portion in said second vessel and a position for opening thereof, respectively.

15. A device for evaluating a water cloud occurring within a lighting chamber of a vehicle lighting fixture, said lighting chamber including a translucent cover and a lamp body formed with vent holes for communicating with an outer space of said lighting chamber, said device comprising:

a partition member partitioning said outer space of said lighting fixture into a front space and a rear space around the outer circumferential portion of said lighting fixture; and vehicle environment simulation setting means for simulatively setting one of said front space and said rear space in a vehicle environment, wherein said vehicle environment simulation setting means comprises at least one simulation setting unit provided in one of said front space and said rear space; and at least one of said at least one simulation setting unit is configured to be movable.

16. The device of claim 15, wherein said environment simulation setting means is configured to simulatively set said front space in a predetermined vehicle outside environment, and said at least one simulation setting unit is provided is said front space.

17. The device of claim 15, wherein said environment simulation setting means is configured to simulatively set said rear space in a predetermined vehicle inside environment, and said at least one simulation setting unit is provided is said rear space.

18. A device for evaluating a water cloud occurring within a lighting chamber of a vehicle lighting fixture, said lighting chamber including a translucent cover and a lamp body formed with vent holes for communicating with an outer space of said lighting chamber, said device comprising:

means for supporting the vehicle lighting fixture within the device;

means for partitioning said outer space of said lighting fixture into a front space and a rear space around an outer circumferential portion of said lighting fixture, wherein said means for partitioning is independent of said means for supporting the vehicle lighting fixture;

vehicle outside environment simulation setting means for simulatively setting said front space in a vehicle outside environment; and vehicle inside environment simulation setting means for simulatively setting said rear space in a vehicle inside environment.

19. The device of claim 18, wherein said means for partitioning includes a predetermined opening portion which is formed in one of a cuttable sheet and a flexible sheet.

20. The device of claim 18, wherein said means for partitioning comprises a sheet and a rigid plate for supporting a circumferential portion of said sheet, and is substantially opaque to visible and near infrared radiation.

* * * * *